US00PP12668P2

(12) United States Plant Patent

Noodelijk

(10) Patent No.: US PP12,668 P2
(45) Date of Patent: Jun. 4, 2002

(54) CHRYSANTHEMUM PLANT NAMED 'EVEREST PINK'

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 09/276,695

(22) Filed: Mar. 26, 1999

(51) Int. Cl.[7] ..... A01H 5/00
(52) U.S. Cl. ..... Plt./297
(58) Field of Search ..... Plt./297, 286

*Primary Examiner*—Bruce R. Campell
*Assistant Examiner*—June Hwu

(57) ABSTRACT

A Chrysanthemum plant named 'Everest Pink' characterized by its medium sized blooms with pale pink ray-florets and yellow-green disc florets.

2 Drawing Sheets

RELATED CULTIVARS

'Everest Pink' is related to 'Everest Salmon' (see copending Ser. No. 09/276,693) and 'Everest White' (see copending Ser. No. 09/276,633). 'Everest Salmon' and 'Everest White' are mutants from 'Everest Pink'.

BACKGROUND OF THE INVENTION

'Everest Pink' is a product of a breeding-program which had the objective of creating new chrysanthemum cultivars with a daisy type flower, a 6.5–7 week response and a short till medium plant height. The new plant of the present invention comprises a new and distinct cultivar of Chrysanthemum plant. 'Everest Pink' is a seedling from a cross in a breeding program maintained under the control of inventor. The female parent is # 90.1402 —unpatented—, an unnamed seedling not available to inventor for description. The male parent is unknown, being a mixed pollation of a group of male parents. The new and distinct cultivar was discovered and selected as a flowering plant within the progeny of the stated cross by Rob Noodelijk in a controlled environment (greenhouse) in Rijsenhout Holland in May 1995. The first act of asexual reproduction of 'Everest Pink' was accomplished when vegetative cuttings were taken from the initial selection in July 1995 in a controlled environment in Rijsenhout Holland.

SUMMARY OF THE INVENTION

The present invention is a new and distinct variety of chrysanthemum bearing medium sized blooms with pale pink ray-florets and yellow-green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
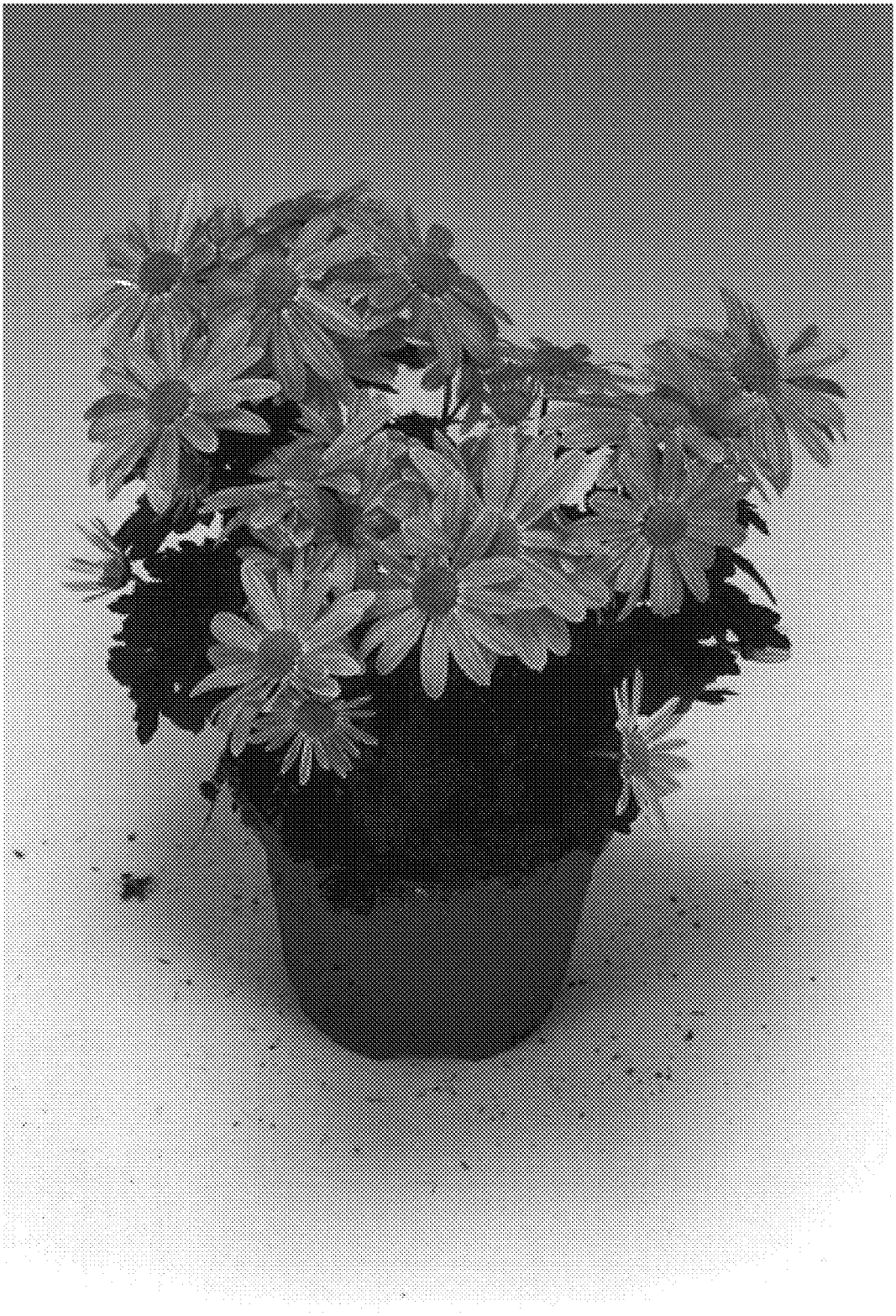
FIG. 1 shows a plant of the cultivar in full bloom.
Figure 2:
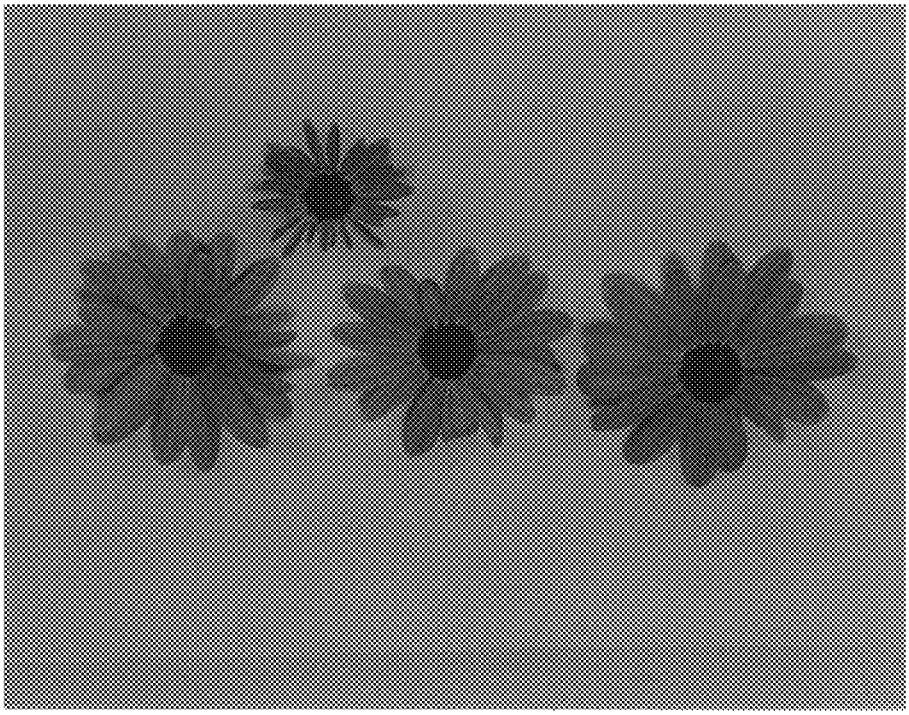
FIG. 2 shows the various stages of bloom of the new cultivar.
Figure 3:
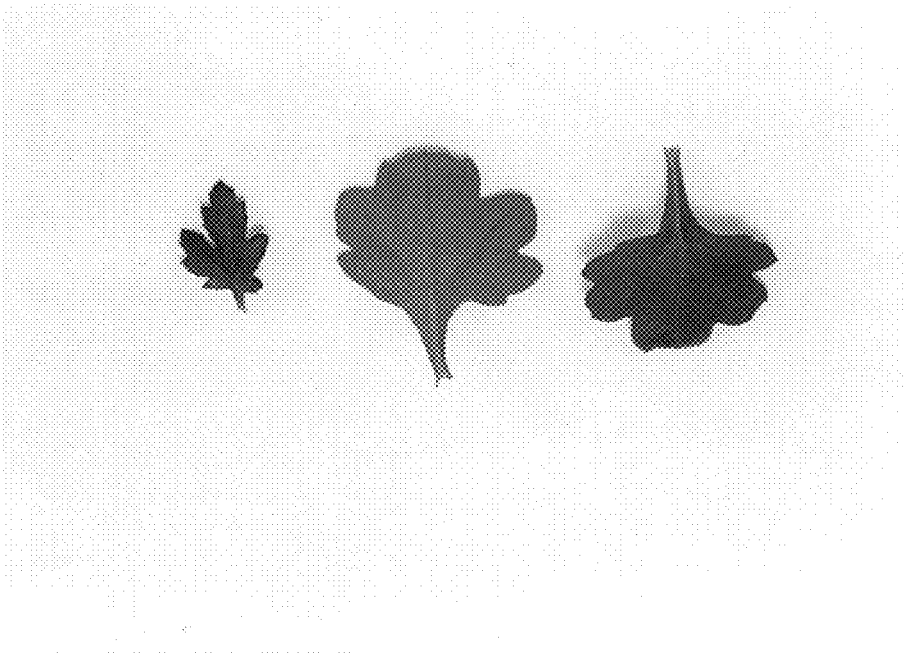
FIG. 3 shows the foliage of the new cultivar.

This new variety of chrysanthemum is of the botanical classification *Dendranthema grandiflora*. The observations and measurements were gathered from plants grown in a greenhouse in Rijsenhout Holland in a photo-periodic controlled crop under conditions generally used in commercial practice. The photo-periodic response time in this crop was 48 days after an average of eight long days. After this long day period to flowering growth retardants were applied 6 times in an average dose of 1.5 gram/liter water. This new variety produces medium sized blooms with pale pink ray-florets and yellow-green disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'Everest Pink' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

From the cultivars known to inventor the most similar existing cultivars in comparison to 'Everest Pink' are 'Everest Salmon' and 'Everest White'. When 'Everest Salmon' and 'Everest White' and 'Everest Pink' are being compared the following differences are noticed: The difference of 'Everest Salmon' and 'Everest White' and 'Everest Pink' is the color of the ray-florets for which characteristic 'Everest Salmon' and 'Everest White' has been selected out of 'Everest Pink'. The color of the ray-florets of 'Everest Pink' is pale pink, the color of the ray-florets of 'Everest Salmon' is salmon and the color of the ray-florets of 'Everest White' is white. All other characteristics of 'Everest Pink', 'Everest Salmon' and 'Everest White' are the same.

The following is a description of the plant and characteristics that distinguish 'Everest Pink' as a new and distinct variety.

The color designations are taken from the plant itself. Accordingly, any discrepancies between the color designations and the colors depicted in the photographs are due to photographic tolerances.

CULTIVAR 'Everest Pink'

Bud:

*Size.*—Small cross-section 0.9 cm, height 0.7 cm.
*Outside color.*—Purple 75 D.
*Involucral bracts.*—2 rows, length 7 mm., width 2 mm.
*Involucral bracts among disc-florets.*—Not present.
*Involucral bracts color.*—Green 138 B.

Bloom:

*Type.*—Daisy.
*Height.*—Flat 2 cm.
*Size.*—Medium.
*Fully expanded.*—6.5–7.0 cm.
*Borne* (*number of blooms per branch*).—Approx. 5 blooms per branch.
*Length of lateral branch.*—From top to bottom approx. 11.0 cm.
*Lateral branch attachment.*—Medium.
*Branching.*—Good with 5 breaks after pinching.
*Performance on the plant.*—5 weeks.
*Seeds.*—Not produced.
*Fragrance.*—Typical chrysanthemum.

Color:

*Center of the flower* (*disc-florets*).—Immature Yellow-green 145 A in the center and yellow 12 A at the border, mature yellow 12 A.
*Color of upper surface of the majority of the ray-florets.*—Purple 75 B with and a little white at the edge.
*Color of the lower surface of the majority of the ray-florets.*—Purple 75 C.
*Tonality from distance.*—A pot mum with pale pink daisy flowers and a yellow-green disc.
*Discoloration to color.*—Purple 75 C.

Ray florets:

*Texture.*—Upper and under side smooth.
*Number.*—16–20 (1 row).
*Cross-section.*—Concave.
*Longitudinal axis of majority. Reflexing.*
*Margin.*—Entire.
*Length of corolla tube.*—Short.
*Ray floret length.*—2.6–2.8 cm.
*Ray floret width.*—0.8 cm.

Disc florets:

*Disc diameter.*—Small (1.2 cm).
*Distribution of disc florets.*—Numerous and clearly visible at all stages of flower head development.
*Type.*—Tubular.
*Color.*—Yellow-green 144B.
*Receptacle shape.*—Conical raised.

Reproductive organs:

*Stamen* (*present in disc florets only*).—Yellow-green 144A, thin, 2 mm in length.
*Pollen.*—None.
*Styles* (*present in both ray and disc florets*).—Yellow-green 144A, thin.
*Style length.*—4 mm.
*Stigmas.*—Yellow-green 144A.
*Stigma width.*—1 mm.
*Ovaries.*—Enclosed in calyx.

Plant:

*Form.*—A pot mum meant for indoor use.
*Growth habit.*—Upright.
*Growth rate.*—Moderate.
*Height.*—18.0–21.0 cm.
*Width.*—Medium, 20.0–22.0 cm.
*Stem color.*—Yellow-green 146 A.
*Stem strength.*—Strong.
*Stem brittleness.*—Present.
*Stem anthocyanin coloration.*—Present to greyed-red along the nodes.
*Flowering response* (*photo-periodic controlled crop, no natural growing*).—48 days.

Foliage:

*Color.*—Upper side yellow-green 147 A under side green 146 A.
*Size.*—Medium, length 6.5 cm, width 5.0 cm.
*Quantity* (*number per lateral branch*).—6–7.
*Shape.*—Ovate.
*Texture upper side.*—Fleshy.
*Texture under side.*—Smooth.
*Ribs and veins upper side.*—Ribs and veins well developed.
*Ribs and veins under side.*—Ribs and veins well developed.
*Venation arrangement.*—Palmate.
*Edge.*—Crenated.
*Shape of base of sinus between lateral lobes.*—Round.
*Margin of sinus between lateral lobes.*—Converging.
*Shape of base.*—Cordate.
*Apex.*—Mucronate.
*Age.*—56 days.

TABLE 2

Differences with comparison varieties

| | 'Everest Pink' | 'Everest Salmon' | 'Everest White' |
|---|---|---|---|
| Color of the upper surface of the majority of the ray-florets | Purple 75 B | Orange-Red 35 D and yellow 10 B at the base | White 155 D |
| Color of the lower surface of the majority of the ray-florets | Purple 75 C | Greyed-Orange 165 D | White 155 D |
| Discoloration to color | To Purple 75 C | To Red 36 C | To White 155D |

I claim:

1. A new and distinct variety of chrysanthemum plant as described and illustrated.

* * * * *